United States Patent
Zhou et al.

[11] Patent Number: 5,792,184
[45] Date of Patent: Aug. 11, 1998

[54] APPARATUS FOR GENERATING ELECTROMAGNETIC RADIATION

[76] Inventors: Lin Zhou; Xue-shan Zhang, both of 21 Carlos Dr., Fairfield, N.J. 07006

[21] Appl. No.: 557,303

[22] Filed: Nov. 14, 1995

Related U.S. Application Data

[63] Continuation-in-part of Ser. No. 374,475, Jan. 17, 1995, and a continuation-in-part of Ser. No. 395,042, Feb. 28, 1995, which is a division of Ser. No. 827,636, Jan. 29, 1992, abandoned, which is a continuation-in-part of Ser. No. 508,302, Apr. 12, 1990, abandoned, which is a continuation-in-part of Ser. No. 103,808, Oct. 1, 1987, abandoned.

[30] Foreign Application Priority Data

May 20, 1987 [CN] China ............................. 87103603
May 20, 1987 [CN] China ............................. 87208158

[51] Int. Cl.[6] ............................................. A61N 5/06
[52] U.S. Cl. ............................ 607/1; 607/80; 607/88; 607/90; 606/3
[58] Field of Search ............................. 600/2; 607/1, 3, 607/80, 88, 90, 91, 94, 95; 606/2, 3

[56] References Cited

U.S. PATENT DOCUMENTS

| | | | |
|---|---|---|---|
| 743,306 | 11/1903 | Merwin | 604/20 |
| 1,429,443 | 9/1922 | McFaddin | 128/395 |
| 3,658,068 | 4/1972 | McNall | 128/395 |
| 3,818,914 | 6/1974 | Bender | 128/396 |
| 3,821,576 | 6/1974 | Larson | 128/395 |
| 3,890,530 | 6/1975 | Hammer et al. | 313/489 |
| 3,967,153 | 6/1976 | Milke et al. | 313/492 |
| 3,995,191 | 11/1976 | Kaduk et al. | 313/489 |
| 4,287,554 | 9/1981 | Wolff | 362/218 |
| 4,420,709 | 12/1983 | Rattray | 313/487 |
| 4,505,545 | 3/1985 | Salia-Manoz | 350/321 |
| 4,540,915 | 9/1985 | Shinkai et al. | 313/486 |
| 4,558,700 | 12/1985 | Mutzhus | 128/395 |
| 4,588,700 | 5/1986 | Mutzhas | 28/395 |
| 4,601,917 | 7/1986 | Russo et al. | 106/287.19 |
| 4,607,191 | 8/1986 | Flaherty | 313/486 |
| 4,663,563 | 5/1987 | Taya et al. | 313/487 |
| 4,716,337 | 12/1987 | Huiskes et al. | 313/487 |
| 4,762,131 | 8/1988 | Okuda | 128/395 |

FOREIGN PATENT DOCUMENTS

| | | | |
|---|---|---|---|
| 1157584 | 5/1958 | France | 128/395 |
| 3027516 | 2/1982 | Germany | 128/395 |

OTHER PUBLICATIONS

"Notices of Judgement Under the FDA", Nov. 1951, p. 467, Federal Register.
"Luminescence of Alkaline–Earth Pyrophosphates, Actuated with Divalent Europium," Aug. 1967, Wanmaker et al. Health Dept. of Yunnan, China "Certificate of the Clinical Application and Basic Research WS–Frey Spect. App–," Jun. 1983.
"Certificate of the Clinical Application and Basic Scientific Research W5–Freq. Spect. App.," Jun. 1983, Health Department of Yunnan, China.

*Primary Examiner*—William E. Kamm
*Assistant Examiner*—Kennedy J. Schaetzle
*Attorney, Agent, or Firm*—Workman, Nydegger & Seeley

[57] ABSTRACT

This apparatus can generate simulated bio-frequency spectrum signals from 0.2 μm–10 mm. The signals are produced by a simulated bio-spectrum generating component when monomer or compounds of one or more chemical elements in the apparatus are excited by a certain form of energy source (such as thermal energy or magnetic energy ). The simulated bio-spectrum signals are broad signals from μm to mm. Through direct exposure to the affected parts of the body, the transiting of energy levels of the molecules, atoms and electrons, is a cause of the regulating and improving of the status of development and survival of living organisms.

26 Claims, 3 Drawing Sheets

APPARATUS FOR GENERATING ELECTROMAGNETIC RADIATION

This application is a CIP of 08/374,475, filed Jan. 17, 1995, and a CIP of 08/395,042, filed Feb. 28, 1995, which is a Div. of 0/827,636, filed Jan. 29, 1992, now abandoned, which is a CIP of 07/508,302, filed Apr. 12, 1990, now abandoned, which is a CIP of 07/103,808, filed Oct. 1, 1987, now abandoned.

FIELD OF THE INVENTION

The present invention relates to apparatus for regulating and improving the status of development and survival of living organisms, more particularly to an apparatus which can generate simulated bio-frequency spectrum signals.

BACKGROUND OF THE INVENTION

The inventors found through experiments that the band of frequency spectrum of living organisms is extremely broad; signals may appear in a band expanding from microns (0.2 µm) to millimeters(10 mm), and including the near infrared, middle infrared, far infrared, and even millimeter waves. Studies show that a living organism is a comprehensive physical field, including magnetic field, infrared radiations, and weak microwaves (mainly millimeter waves). That is to say, the living organisms possess a physical field having certain frequencies and a spectrum which is called "bio-frequency spectrum" or "bio-spectrum" by the inventor.

Up to now, people have tried various physical methods to control or affect the status of development and survival of living organisms, such as electrotherapy, ultrasound, infrared ray, ultroviolet ray, microwave, and laser which are frequently used on medical treatment. All these methods are practised in single frequency or very limited band, although each of them uses a different physical elementary particle to treat diseases which results in the making of only one of molecular, atom and electron transit energy level in most cases. While it can produce a partial effect in living organisms, however, the biological effect is always in lower energy levels.

For example, the ultrasound therapeutic apparatus produces sound waves with frequencies over 20,000 Hz; infrared therapeutic apparatus produces infrared radiation with wavelengths of 0.72–25 µm; ultraviolet therapeutic apparatus produces ultraviolet rays with wavelengths of 180–380 nm; microwave therapeutic apparatus produces ultrahigh frequency electromagnetic waves with wavelengths of 1–100 mm; while laser treatments use monochromatic laser light to irradiate the human body. All these methods have deficiencies in biological effects. The reason is that the narrow spectrum does not match with the bio-spectrum of living organisms.

SUMMARY OF THE INVENTION

Therefore, the object of the invention is to provide an apparatus for regulating and improving the status of development and survival of living organisms which can generate simulated bio-frequency spectrum signals with wavelengths of 0.2 µm–10 mm.

According to the present invention the apparatus for regulating and improving the status of development and survival of organisms comprises;

Energy generating means; simulated bio-spectrum signal generating device for receiving the energy generated by the energy generating means and generating simulated bio-spectrum signals with wavelengths of 0.2 µm–10 mm; the simulated bio-spectrum signal generating means comprises one or several monometric chemical elements or their compounds which are capable of generating the simulated bio-spectral signals.

According to the present invention, the apparatus has two features:

1. The apparatus can produce a very broad electromagnetic radiation spectrum which covers visible light band, near and far infrared band, ultra-far infrared band, submillimeter wave band, millimeter wave and possibly, centimeter wave band, i.e. completely covers the frequency wave band of the inherent oscillations of organisms.

2. The electromagnetic radiations are different on intensity at different bands of spectrum, wherein visible light, near, middle, and far infrared account for more than 90% of the radiated energy. While ultrafar infrared, submillimeter wave and millimeter waves occupy a very broad frequency but a very small amount of radiant energy.

BRIEF DESCRIPTION OF THE DRAWINGS

FIGS. 5A–5C shows the application of the present invention for regulating and improving the status of development and survival of living organisms.

DETAILED DESCRIPTION OF THE PREFERRED EMBODIMENT

Figure 1:
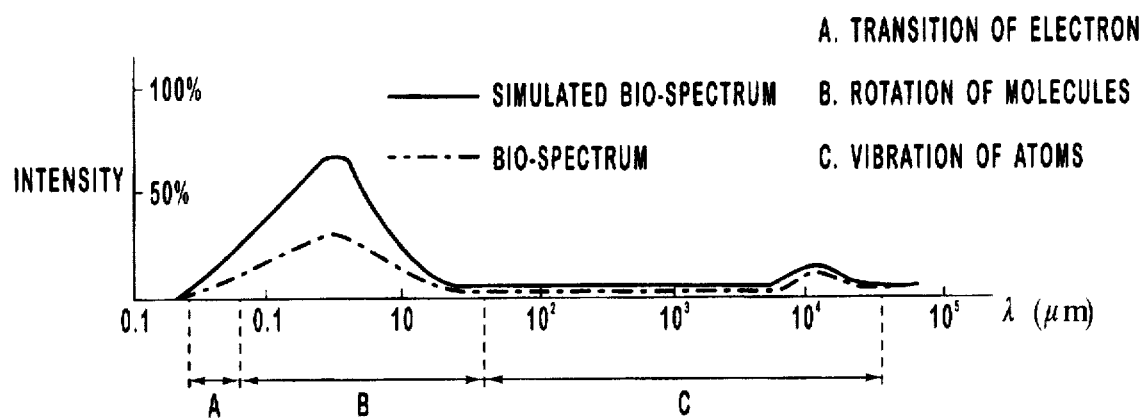
FIG. 1 schematically shows the inherent bio-frequency spectrum of living organism and the simulated bio-frequency spectrum produced by the present invention.

In FIG. 1, the broken line denotes the range of distribution of the inherent bio-spectrum, with wavelengths ranging from 0.2 µm to 100,000 µm. The solid line denotes the simulated bio-spectrum generated according to the present invention, wherein 0.45–0.72 µm is the range from ultraviolet to visible light; 0.72–20 µm is the range of middle infrared; and 20 µm-several cm is the range from far infrared to millimeter waves.

Figure 3:
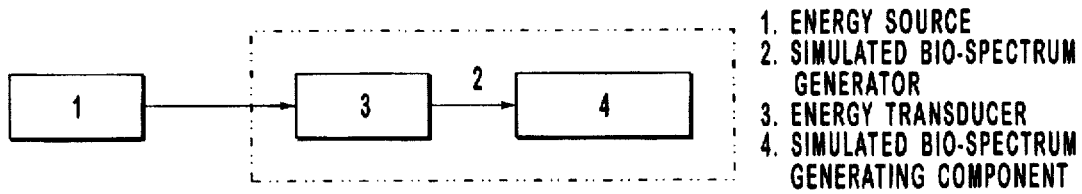
FIG. 3 is the schematic diagram showing the apparatus for regulating and improving the status of development and survival of living organism according to the present invention.

FIG. 3 is the apparatus for regulating and improving the status of development and survival of living organism according to the present invention. In FIG.3, 1 represents an energy source; 3 represents an energy transducer; 4 represents simulated bio-spectrum generating component; energy transducer 3 and generating component 4 constitute the simulated bio-spectrum generator 2. Energy 1 source can be of many forms, such as electrical energy, thermal energy, magnetic energy, solar energy, chemical energy, or biological energy, etc. Electrical energy is preferable because it is easy to acquire. Energy source energy is transduced into thermal or magnetic energy by energy transducer 3 to provide energy to the simulated bio-spectrum generating component 4. The simulated bio-spectrum generating component 4 is composed of monomer or compounds of one or more chemical elements in the periodic table. Upon excitation by energy, the transitions of energy levels of the elements or compounds are emitted in the form of electromagnetic radiation to form a physical field of simulated bio-spectrum and act on living organisms through irradiation. When it matches with the strong absorption band of the organism, a large portion of the radiant energy carried by the electromagnetic wave is absorbed, causing changes of the energies of molecules, atoms, or electrons in living organisms, which then elicits oscillation, enhances bio-oxidation and improves energy of the cells to increase the permeability of the cell membrane.

The chemical elements to be used in the simulated bio-spectrum generator are selected in accordance with the following principles:

a. The spectrum of irradiation of the chemical elements after acquiring energy should be distributed as widely as possible between the micrometer band and the millimeter band. If the irradiation is only in the micrometer(infrared)band or only in the millimeter band, the biological effects produced are not good enough. In order to make the produced biological effects favorable to the growth and development of living organisms, radiant signals should be present all over the range from micrometers to millimeters. Therefore, a broad spectrum of μm-mm is a distinct feature of the present invention. Selection and proportion of the chemical elements are indispensable to the realization of the broad frequency spectrum and are based on the fact that the elements must be able to generate a spectrum approximating the bio-spectrum when excited by energy.

b. The elements should be technically as similar to the chemical constituents of the bio-substances in the living organism as possible. The frequency distribution of the inherent bio-spectrum of living organism is then considered.

The chemical elements that the present invention concerns include most of the elements of the 2nd, 3rd, 4th, and 5th periods of the Mendeleev periodical table, and the rare earth elements of the lanthanium and actinium series. Most of these elements are metal elements and are used in the form of oxides, fluorides, nitrides, sulfides, borides, or carbides, preferably oxides.

To generate the simulated bio-spectrum that best resembles the inherent bio-spectrum as shown in FIG. 1, it is preferable to select one of the following elements or their compounds "Co, Cu, Mo, Li, Be, B, Mg, Al, Si, K, Ca, Ti, V, Cr, Mn, Fe, Ni, Zn, Ge, Sr, Zr, Nb, Ta, Hf, Se, Tn, W, Ge, Au, and Y.

Whenever any one of the following elements or their compounds is taken as the main constituent of the simulated bio-spectrum generating component, its content is preferably not less than 10%;

Cr, Mg, Se, Ge, Zn, Cu, Mn, Al, Sr, Ce, Y, Ca, Zr, Ti, Co, Mo, Si, Fe, V.

The principle of determining the proportions of the above chemical constituents is that their spectrum should be as similar to the spectrum of the subject organism as possible. That is to say, the simulated bio-spectrum should overlap with the bio-spectrum; the more the overlap, the better. For complicated organisms, such as human beings or animals, the spectrum, to be simulated with the constituents in certain proportions should be as broad as possible. It is preferable to cover visible light, infrared through millimeter waves, so that sufficient transitions of the molecules, atoms and electrons can be elicited simultaneously.

The applicants finds whatever the proportions of the chemical elements may be, the key point is whether the spectrum signal generated by the simulated bio-spectrum generator and the energy elicited by the electrons or the excited molecules can be utilized to achieve biological effects of beneficial regulation. A spectrum range of 0.2 μm–10 cm covers most of the bio-spectrum.

Figures 1, 4A:
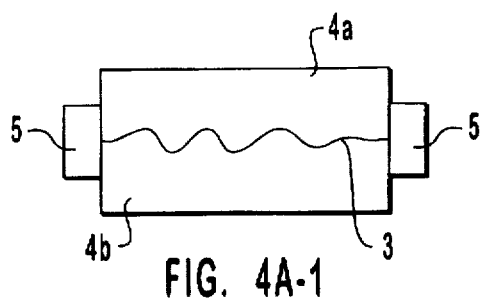
FIGS. 4A–4D are embodiments of the simulated bio-frequency spectrum generator according to the present invention.
Figures 2, 4A:
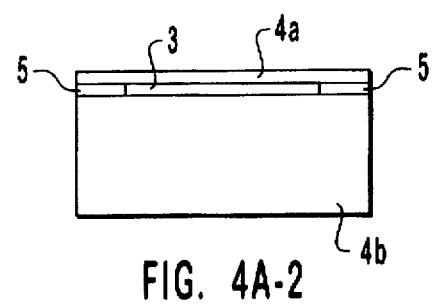

FIG. 4A–4D show the embodiments of the simulated bio-spectrum generator according to the present invention. In FIG. 4A-1, the simulated bio-spectrum generating component 4 comprises a substrate 4B and an emitting layer 4A disposed on the substrate and composed of borides, nitrides, carbides, sulfides or fluoride. 5 is the electrode. The proportions of these elements and their compounds are determined by the kind of organism to be regulated and its status of growth. Material of the substrate is selected according to the type of energy source which is an electric power source in this embodiment. The substrate can be made from non-metal materials, such as ceramics with low hygroscopic properties, high heat resistance, high mechanical strength, high radiance, or heat resistant(<150° C.) plastics with high radiance or quartz glass, micro crystal glass or other kinds of glass with high heat resistance and high strength. It can also be made from electric materials such as carbon rod or resistors which have high electric conductivity and are capable of reaching heat producing temperatures. Various kinds of chemical elements and their compounds are mixed in the right proportion, and then diluted into liquid adhesive, or they may be made into coating material or enamel pulp and coated onto the surface of the substrate to form the emitting layer. Energy transducer 3 can be an electric heating wire or the like which is embedded into the substrate (as shown)or disposed on the ends of the substrate to convert electric energy into thermal energy. The heat generated by the heating wire is used to excite the chemical elements in the emitting layer. The temperature should not be lower than the body temperature of the living organisms.

Figure 2:
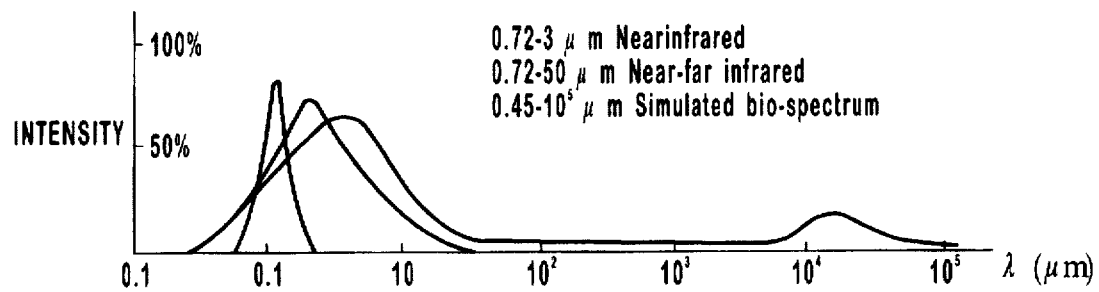
FIG. 2 schematically shows the simulated bio-frequency spectrum produced by the present invention and the spectrum produced by the conventional physical means.

The heating wire 3 in FIG. 4A-1 can be replaced by a layer of conducting membrane 3 (FIG. 4A-2)formed on the surface of the substrate by means of metal oxidation technique (high temperature hydrolysis of chlorides to form a conducting membrane of metal oxides ) to make the simulated bio-spectrum generator more solidified thus increasing the speed and efficiency with which the electric energy is converted into thermal energy (FIG. 4A-1). In FIG. 4A-2, the emitting layer 4A is coated on the surface of the conducting membrane.

Figures 1, 4B:
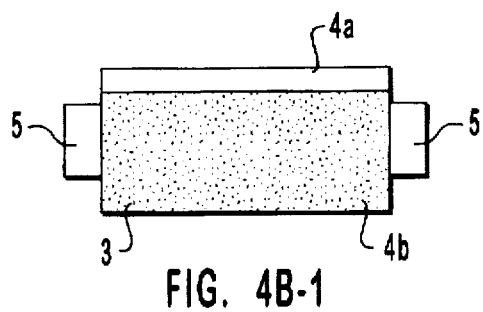
Figures 2, 4B:
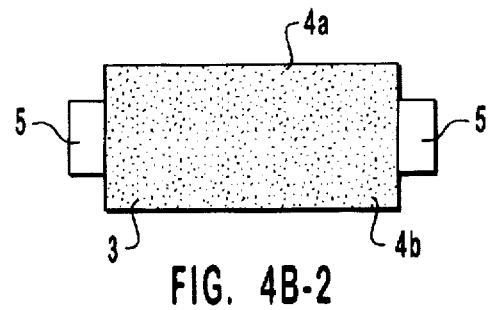

FIG. 4B-1 is another embodiment of the simulated bio-spectrum generator according to the present invention. In this embodiment, substrate 4b is integrated with the energy transducer 3 in a manner that the conducting substance is infiltrated into non-metal material to make it electrically conductive and have satisfactory resistance. The emitting layer 4A is then coated onto the substrate to form a simulated bio-spectrum generator. The substrate can also be made from metals. In this case, electric current introduced into the substrate is converted into thermal energy and the substrate acts as the energy transducer at the same time. Then a layer of enamel pulp mingled with one or more chemical elements and their compounds in the right proportion is coated onto the metal substrate and sintered under high temperature to form a simulated bio-spectrum generator of the metal substrate.

In FIG.4B-2, the chemical elements and their compounds constituting the emitting layer 4A can also be doped into substrate 4B and then sintered under high temperature to form a simulated bio-spectrum generator(FIG. 4B-2) which is even more integral than that of FIG. 4B-1, as shown in FIG. 4B-2.

Figures 1, 4C:
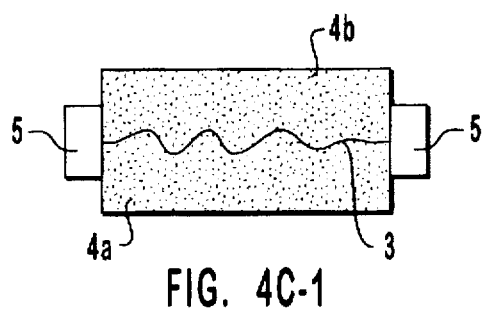
Figures 2, 4C:
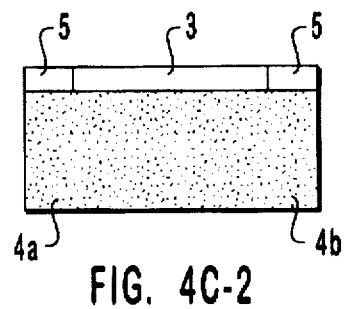

FIG. 4C-1 is still another embodiment of the simulated bio-spectrum generator according to the present invention. In this embodiment, one or more chemical elements and their compounds are mixed in the right proportion with potclay and sintered into an integral body so that the substrate per se contains the constituents that generate the simulated bio-spectrum. When an energy transducer such as electric heating wire is embedded into the substrate, an integrated simulated bio-spectrum generator is formed.

In FIG. 4C-2, a conducting membrane 3 can be plated onto the surface of the substrate 4B containing the chemical elements of the emitting layer 4A. The conducting membrane 3 replaces the heating wire 3, and makes the simulated bio-spectrum generator a more integral body as shown in FIG. 4C-2.

Figure 4D:
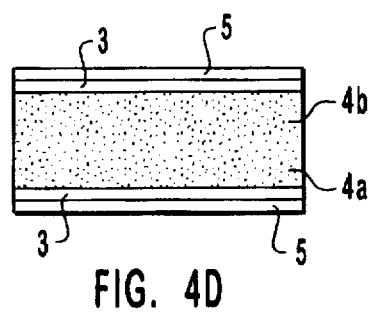
Figure 5A:
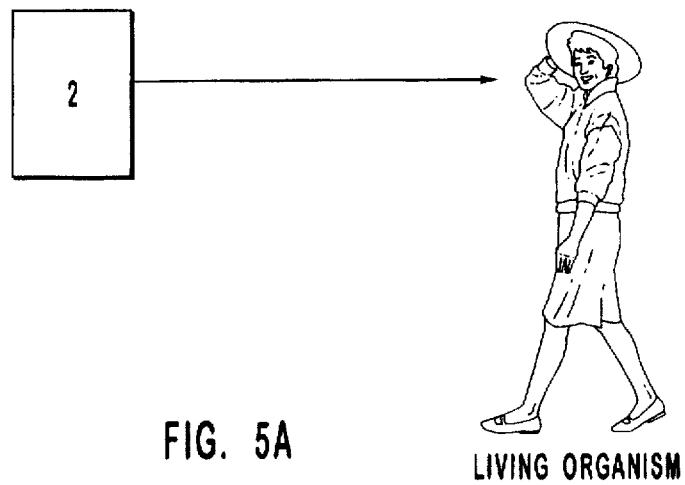
Figure 5B:
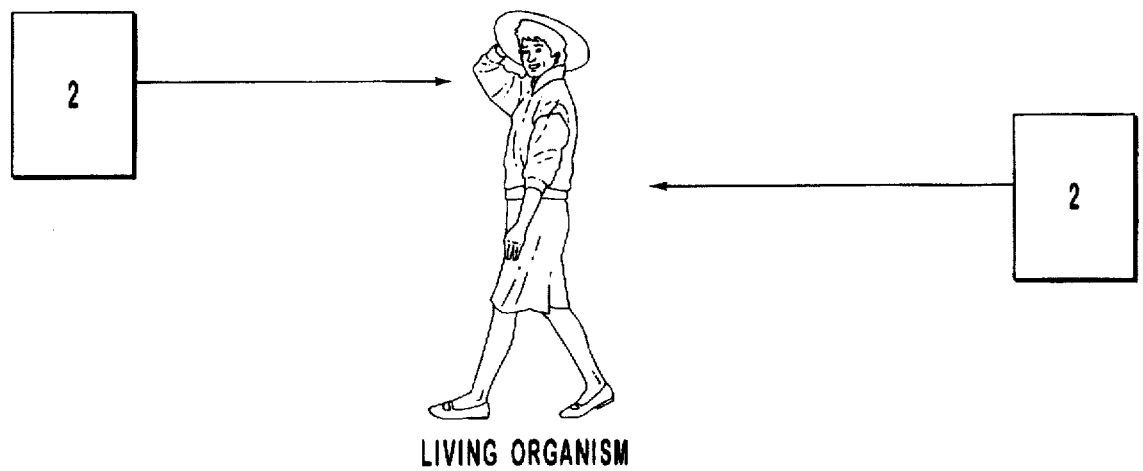
Figure 5B:
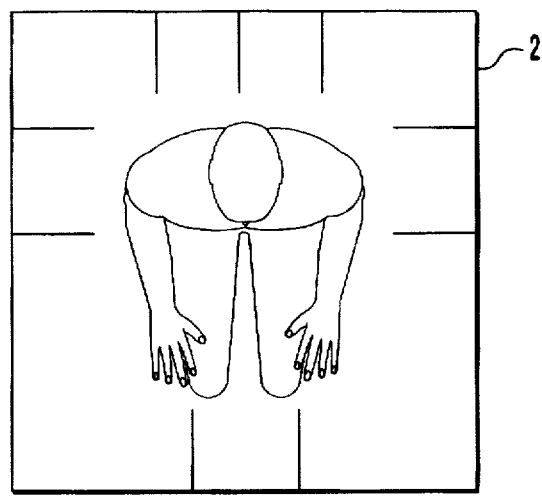

FIG. 4D is still another embodiment of the simulated bio-spectrum generator according to the present invention. In this embodiment, temperature resisting glass is used as the material of the substrate and one or more chemical elements and their compounds are mixed in the right proportion into the raw glass during sintering. A special glass body containing the constituents that generate the simulated bio-spectrum is formed by sintering. Then a layer of semiconductor membrane is formed on the surface of the glass as the energy transducer by means of the metal oxidation, thus forming a colorless and transparent simulated bio-spectrum generator. In this embodiment, the material of the substrate can also be pot clay containing one or more chemical elements and their compounds so that the substrate per se contains constituents that generate the simulated bio-spectrum. An integrated solid ceramic simulated bio-spectrum generator is formed by disposing a layer of conducting membrane of metal oxides on the surface of such a substrate as an electrically conducting energy transducer.

The substrate can be made from either permanent or electric magnetic materials. In this case, the emitting layer is plated onto the magnetic substrate and the non-thermal simulated bio-spectrum generator made from magnetic material is formed.

We claim:

1. An apparatus for generating electromagnetic radiation comprising:
   means for supplying energy;
   means for converting energy supplied by said means for supplying energy into at least one of thermal and magnetic energy; and
   means for generating a first electromagnetic radiation and a second electromagnetic radiation when excited by said at least one of thermal and magnetic energy produced by said means for converting energy, the first electromagnetic radiation having a wavelength in range from about 0.2 μm to about 50 μm, and the second electromagnetic radiation having a wavelength in range from about 7500 μm to about 100,000 μm, and wherein the means for generating the first electromagnetic radiation and the second electromagnetic radiation generates substantially no electromagnetic radiation having a wavelength in a range from about 50 μm to about 7500 μm.

2. The apparatus according to claim 1, wherein said means for supplying energy is an electric power source.

3. The apparatus according to claim 1, wherein said means for generating a first electromagnetic radiation and a second electromagnetic radiation comprises a non-metal substrate, a layer substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V upon the surface of said substrate, and an electrothermal converting means provided within said substrate.

4. The apparatus according to claim 1, wherein said means for generating a first electromagnetic radiation and a second electromagnetic radiation comprises a non-metal substrate, a conducting membrane of metal oxides plated onto the surface of said substrate to form an electrothermal energy converting means; and a layer substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V coated on the surface of said conducting membrane of metal oxides.

5. The apparatus according to claim 1, wherein said means for generating a first electromagnetic radiation and a second electromagnetic radiation comprises a non-metal substrate containing therein a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V, and an electrothermal energy converting means.

6. The apparatus according to claim 1, wherein said means for generating a first electromagnetic radiation and a second electromagnetic radiation comprises a non-metal substrate containing therein a composition of which at least 10% ther element selected from a group consisting of: Cr, Mg, Se, Ge, Zn, Cu, Mn, Al, Sr, Ce, Y, Ca, Zr, Ti, Co, Mo, Si, Fe, and V, and electrically conducting substances for converting electrical energy to thermal energy.

7. The apparatus according to claim 1, wherein said means for generating a first electromagnetic radiation and a second electromagnetic radiation comprises a metal substrate, and a layer composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V and placed directly onto the surface of the substrate.

8. The apparatus according to claim 1, wherein said means for generating a first electromagnetic radiation and a second electromagnetic radiation comprises a substrate made from high temperature resistant glass containing therein a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V, and a layer of electrically conducting membrane made from metal oxides and formed on a surface of the substrate for converting electrical energy to thermal energy.

9. The apparatus according to claim 1, wherein said means for supplying energy is a source of a magnetic field; and wherein said means for generating a first electromagnetic radiation and a second electromagnetic radiation comprises a substrate made from magnetic material and having thereon a coating composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V.

10. The apparatus as defined in claim 1, wherein the first electromagnetic radiation is at least ninety percent of the electromagnetic radiation generated by the means for generating the first electromagnetic radiation and the second electromagnetic radiation.

11. The apparatus as defined in claim 1, wherein the means for generating the first electromagnetic radiation and the second electromagnetic radiation has an electromagnetic radiation generator component substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V.

12. The apparatus as defined in claim 1, wherein the means for converting energy supplied by said means for supplying energy converts energy supplied by said means for supplying energy into magnetic energy.

13. An apparatus for generating electromagnetic radiation comprising:

means for supplying energy;

means for converting energy supplied by said means for supplying energy into at least one of thermal and magnetic energy; and means for generating a first electromagnetic radiation and a second electromagnetic radiation when excited by said at least one of thermal and magnetic energy produced by said means for converting energy, wherein:

the first electromagnetic radiation has a wavelength in range from about 0.2 μm to about 50 μm;

the second electromagnetic radiation has a wavelength in range from about 7500 μm to about 100,000 μm;

the first electromagnetic radiation is at least ninety percent of the electromagnetic radiation generated by the means for generating the first electromagnetic radiation and the second electromagnetic radiation, and the means for generating the first electromagnetic radiation and the second electromagnetic radiation generates substantially no electromagnetic radiation having a wavelength in a range from about 50 μm to about 7500 μm.

14. The apparatus as defined in claim 13, wherein the means for generating the first electromagnetic radiation and the second electromagnetic radiation has an electromagnetic radiation generator component substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V.

15. The apparatus as defined in claim 13, wherein the means for generating the first electromagnetic radiation and the second electromagnetic radiation has an electromagnetic radiation generator component substantially composed of a composition selected from a group consisting of: Co, Cu, Mo, Li, Be, B, Mg, Al, Si, K, Ca, Ti, V, Cr, Mn, Fe, Ni, Zn, Ge, Sr, Zr, Nb, Ta, Hf, Se, Tn, W, Ge, Au, Y, and compounds thereof.

16. The apparatus according to claim 13, wherein the means for converting energy supplied by said means for supplying energy converts energy supplied by said means for supplying energy into magnetic energy.

17. An apparatus for generating electromagnetic radiation comprising:

means for supplying energy;

means for converting energy supplied by said means for supplying energy into at least one of thermal and magnetic energy; and means for generating electromagnetic radiation when excited by said at least one of thermal and magnetic energy produced by said means for converting energy, the means for generating electromagnetic radiation having an electromagnetic radiation generator component substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V;

wherein the electromagnetic radiation generated by said means for generating electromagnetic radiation comprises:

at least ninety percent thereof being a first electromagnetic radiation having a wavelength in range from about 0.2 μm to about 50 μm;

greater than zero percent but less than ten percent being a second electromagnetic radiation having a wavelength in range from about 7500 μm to about 100,000 μm; and substantially no electromagnetic radiation having a wavelength in a range from about 50 μm to about 7500 μm.

18. The apparatus as defined in claim 17, wherein the means for converting energy supplied by said means for supplying energy converts energy supplied by said means for supplying energy into magnetic energy.

19. An apparatus for generating heat and electromagnetic radiation to provide a therapeutic effect to a human being, the apparatus comprising:

electrical leads for receiving electrical power;

a substrate;

a volume of a material situated upon the substrate, the volume of the material being in communication with the electrical leads for being electrically resistance heated by the electrical power received from the electrical leads such that the material generates heat and electromagnetic radiation when electrically resistance heated, wherein the electromagnetic radiation generated by the electrically resistance heated material comprises:

at least ninety percent thereof being a first electromagnetic radiation having a wavelength in range from about 0.2 μm to about 50 μm;

greater than zero percent but not more than ten percent thereof being a second electromagnetic radiation having a wavelength in range from about 7500 μm to about 100,000 μm; and substantially no electromagnetic radiation having a wavelength in a range from about 50 μm to about 7500 μm;

whereby the heat and the electromagnetic radiation generated by the electrically resistance heated material provides a therapeutic effect in the heating and radiating of a living human being.

20. The apparatus as recited in claim 19, wherein the material is substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V.

21. An apparatus for generating heat and electromagnetic radiation to provide a therapeutic effect to a living organism, the apparatus comprising:

an electrical conduit for receiving electrical power;

a substrate;

a volume of a material situated upon the substrate, the volume of the material being in communication with the electrical conduit for being electrically resistance heated by the electrical power received from the electrical conduit such that the material generates heat and electromagnetic radiation when electrically resistance heated, wherein the electromagnetic radiation generated by the electrically resistance heated material comprises:

greater than ninety percent thereof being a first electromagnetic radiation having a wavelength in range from about 0.2 μm to about 50 μm;

less than ten percent but greater than zero percent thereof being a second electromagnetic radiation having a wavelength in range from about 7500 μm to about 100,000 μm; and substantially no electromagnetic radiation having a wavelength in a range from about 50 μm to about 7500 μm;

whereby the heat and the electromagnetic radiation generated by the electrically resistance heated material provides a therapeutic effect in the heating and radiating of a living organism.

22. The apparatus as recited in claim 21, wherein the material is substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V.

23. An apparatus for generating heat and electromagnetic radiation to provide a therapeutic effect to a living organism, the apparatus comprising:

an electrical conduit for receiving electrical power;

a substrate;

a volume of a material situated upon the substrate, the volume of the material being in communication with the electrical conduit for being electrically resistance heated by the electrical power received from the electrical conduit such that the material generates heat and electromagnetic radiation when electrically resistance heated, wherein the electromagnetic radiation generated by the electrically resistance heated material comprises:

at least ninety percent thereof being a first electromagnetic radiation having a wavelength in range from about 0.2 μm to about 50 μm; and greater than zero percent thereof being a second electromagnetic radiation having a wavelength in range from about 7500 μm to about 100,000 μm;

whereby the heat and the electromagnetic radiation generated by the electrically resistance heated material provides a therapeutic effect in the heating and radiating of a living organism.

24. The apparatus as recited in claim 23, wherein the material is substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V.

25. An apparatus for generating heat and electromagnetic radiation to provide a therapeutic effect to a living organism, the apparatus comprising:

an electrical conduit for receiving electrical power;

a substrate;

a volume of a material situated upon the substrate, the volume of the material being in communication with the electrical conduit for being electrically resistance heated by the electrical power received from the electrical conduit such that the material generates heat and electromagnetic radiation when electrically resistance heated, wherein the electromagnetic radiation generated by the electrically resistance heated material comprises:

a majority thereof being a first electromagnetic radiation having a wavelength in range from about 0.2 μm to about 50 μm; and greater than zero percent thereof being a second electromagnetic radiation having a wavelength in range from about 7500 μm to about 100,000 μm;

whereby the heat and the electromagnetic radiation generated by the electrically resistance heated material provides a therapeutic effect in the heating and radiating of a living organism.

26. The apparatus as recited in claim 25, wherein the material is substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V.

* * * * *

UNITED STATES PATENT AND TRADEMARK OFFICE
CERTIFICATE OF CORRECTION

PATENT NO. : 5,792,184
DATED : Aug. 11, 1998
INVENTOR(S) : Lin Zhou Xue-shan Zhang It is certified that error appears in the above-indentified patent and that said Letters Patent is hereby corrected as shown below:

Cover Page, Right Column, Other Publications, line 6, after "Basic" inert --Scientific-- and after "WS" change "Frey" to --Freq--

Col. 2, lines 53 and 54, change numbers "1, 3, and 4" to --1, 3, and 4--

Col. 3, line 66, after "The" change "applicants" to --applicant--

Col. 6, line 24, after "10%" change "ther" to --thereof is an--

Signed and Sealed this

Twenty-eighth Day of September, 1999

*Attest:*

Q. TODD DICKINSON

*Attesting Officer*  *Acting Commissioner of Patents and Trademarks*